United States Patent [19]
Okamoto et al.

[11] Patent Number: 5,679,572
[45] Date of Patent: Oct. 21, 1997

[54] SEPARATION OF CHIRAL COMPOUNDS ON POLYSACCHARIDE SUPPORTS

[75] Inventors: Yoshio Okamoto, Nagoya; Naoki Enomoto, Aichi-ken; Ryu Ohishi, Handa; Yasushi Ogasawara, Hekinan; Hirofumi Akano, Handa; Yoshiya Kawamura, Khonan, all of Japan

[73] Assignee: Daicel Chemical Industries, Ltd., Osaka, Japan

[21] Appl. No.: 239,698

[22] Filed: May 9, 1994

[30] Foreign Application Priority Data

Sep. 22, 1993 [JP] Japan .................. 5-257538

[51] Int. Cl.$^6$ .................. B01D 15/08; G01N 30/48; C01B 33/12
[52] U.S. Cl. .................. 435/803; 210/730; 436/161; 536/123.1; 536/124; 502/232
[58] Field of Search .................. 536/1.11, 4.1, 536/18.7, 22.1, 115, 124, 123.1; 502/232; 435/803; 210/730; 436/161

[56] References Cited

U.S. PATENT DOCUMENTS

| | | | |
|---|---|---|---|
| 4,619,970 | 10/1986 | Okamoto et al. | 536/56 |
| 4,818,394 | 4/1989 | Okamoto et al. | 536/64 |
| 4,861,872 | 8/1989 | Okamoto et al. | 536/18.7 |
| 4,912,205 | 3/1990 | Okamoto et al. | 536/18.7 |
| 5,032,277 | 7/1991 | Okamoto et al. | 210/635 |
| 5,051,500 | 9/1991 | Elmore | 536/124 |
| 5,071,978 | 12/1991 | Sau | 536/124 |
| 5,202,433 | 4/1993 | Okamoto et al. | 536/18.7 |
| 5,371,208 | 12/1994 | Kozulic | 536/1.11 |

FOREIGN PATENT DOCUMENTS

| | | |
|---|---|---|
| 147804 | 7/1985 | European Pat. Off. |
| A-0 445 604 | 9/1991 | European Pat. Off. |
| 527234 | 2/1993 | European Pat. Off. |
| A-0 625 524 | 11/1994 | European Pat. Off. |
| 62-270602 | 11/1987 | Japan |

OTHER PUBLICATIONS

Elisabeth Kallin et al, "New Derivatization and Separation Procedures for Reducing Oligosaccharides", Glycoconjugate J. 1986 3, 311–319.

Yoshio Okamoto et al, "Tris(4–t–butylphenylcarbamate)s of Cellulose and Amylose as Useful Chiral Stationary Phases for Chromatographic Optical Resolution", Chemistry Letters (1989), pp. 715 to 718.

Patent Abstracts of Japan, vol. 12, No. 159, 14 May 1988 of JP–A–62 270602, 25 Nov. 1987, & Database WPI, Week 8802, Derwent Publications Ltd., London, GB; AN 009299.

Manssur Yalpani, "Polysaccharides", 1988, Elsevier, Amsterdam, pp. 294–297. Month not available.

S. Kim et al, "Copolymers of Depolymerized Cellulose Triacetate and Diisocyanates", vol. 7, 1979, New York, pp. 101–105. Month not available.

*Primary Examiner*—Gary L. Kunz
*Attorney, Agent, or Firm*—Frishauf, Holtz, Goodman, Langer & Chick, P.C.

[57] ABSTRACT

Provided is a novel polysaccharide derivative having a main structure of the following formula (1) in which a polysaccharide or its derivative has been chemically bonded to the inner and outer surfaces of the pores of a porous carrier at the reducing terminal of the polysaccharide or polysaccharide derivative:

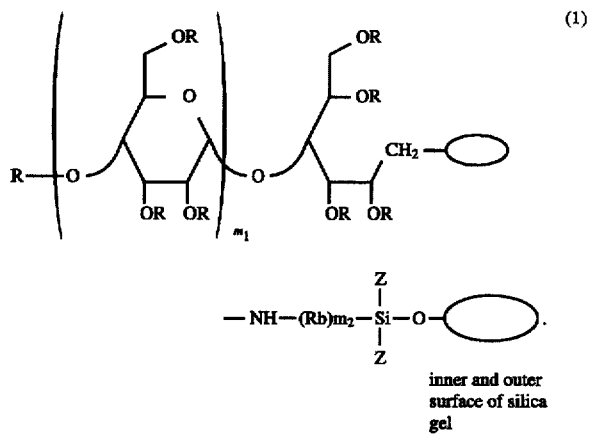

inner and outer surface of silica gel

Also provided are a method of producing the novel polysaccharide derivative in which a silane agent is chemically bonded to a porous carrier and thereafter a polysaccharide having a degree of polymerization from 11 to 500 or its derivative is further chemically bonded to surface treated carrier at the reducing terminal of the polysaccharide or its derivative, and a method of producing the novel polysaccharide derivative in which a polysaccharide having a degree of polymerization from 11 to 500 or its derivative is chemically bonded to a silane agent at the reducing terminal of the polysaccharide or its derivative and thereafter the polysaccharide derivative is further chemically bonded to a porous carrier. Further provided is a separating agent for chromatography containing the novel polysaccharide derivative. The novel polysaccharide derivative has excellent solvent resistance and is useful as a separating agent for chiral resolution of chiral compounds by chromatography. The methods of the present invention efficiently give the novel polysaccharide derivative.

18 Claims, No Drawings

SEPARATION OF CHIRAL COMPOUNDS ON POLYSACCHARIDE SUPPORTS

FIELD OF THE INVENTION

The present invention relates to novel polysaccharide derivatives, methods of producing them and use of them. More precisely, it relates to novel polysaccharide derivatives where a silane agent and a porous silica gel carrier have been chemically bonded to each other and a polysaccharide has been bonded to the resulting compound at its reducing terminal and where particular substituent(s) has/have been introduced into a part or all of the hydroxyl groups in the polysaccharide moiety, and also to methods of producing them and use of them.

BACKGROUND OF THE INVENTION

It has heretofore been known that a separating agent comprising a compound where silica gel has been modified to physically carry a polysaccharide, such as cellulose or amylose, or a derivative thereof is useful for optical resolution.

However, since the compound has poor solvent resistance, it has such a drawback that, when it is used in liquid chromatography or the like, it limits the usable eluent. In addition, the usefulness of the polysaccharide cannot sufficiently be drawn out of it and it limits also the washing solution that is to be used for washing contaminated columns, by which the columns are often deteriorated.

In order to overcome the problems, it has been proposed to use a compound where a polysaccharide derivative has been chemically bonded to silica gel. In the compound, however, since the site of the polysaccharide derivative, to which silica gel is to be chemically bonded, cannot be specifically defined, the bonded silica gel has an influence on the higher structure of the polysaccharide itself to lower the useful properties of the polysaccharide. Hence, the compound has such a serious problem. In addition, since the bonding site of the polysaccharide derivative cannot be specifically defined, there occurs still another problem that the unevenness in the quality of the silica gel compound to be obtained is noticeable.

We, the present inventor already solved the above-mentioned problems, using silica gel as the porous carrier where polysaccharides are bonded to the inner and outer surfaces of the pores of the silica gel at their reducing terminals by amide bond. However, in order to produce the compound, the reducing terminal of the polysaccharide which is to be bonded to silica gel must be lactonated. In this case, since the direct lactonation of the reducing terminal of a polysaccharide is difficult, the corresponding oligosaccharide is previously lactonated and then the saccharide chain of the lactonated oligosaccharide is polymerized by enzymatic reaction. For these reasons, this method has the following problems.

(1) If there is no synthetase capable of polymerizing the useful oligosaccharides to polysaccharides, compounds useful as a separating agent cannot be produced.

(2) Even if there are some useful enzymes, the purification of the enzymes is difficult.

(3) The enzymes and the enzyme substrates are expensive and the method of using them is not practical.

(4) The reaction steps are complicated.

SUMMARY OF THE INVENTION

Given this situation, we, the present inventors have noted the direct utilization of polysaccharides and have found for the first time a method of bonding silica gel that has been surface-treated to have amino groups to a polysaccharide at the carbonyl group in its reducing terminal by chemical bond, in the presence of a reducing agent, to produce the intended compound. On the basis of the finding, we have completed the present invention.

According to the method, a novel compound of the following general formula (1) is obtained, in which the polysaccharide has been chemically bonded to the inner and outer surfaces of the pores of the porous carrier only at the 1-position carbon in the reducing terminal of the saccharide moiety via a silanizing reagent.

Specifically, there is provided in accordance with the present invention a novel polysaccharide derivative having a main structure of the following general formula (1) in which a polysaccharide or its derivative has been chemically bonded to the inner and outer surfaces of the pores of silica gel at the reducing terminal of the polysaccharide or polysaccharide derivative site.

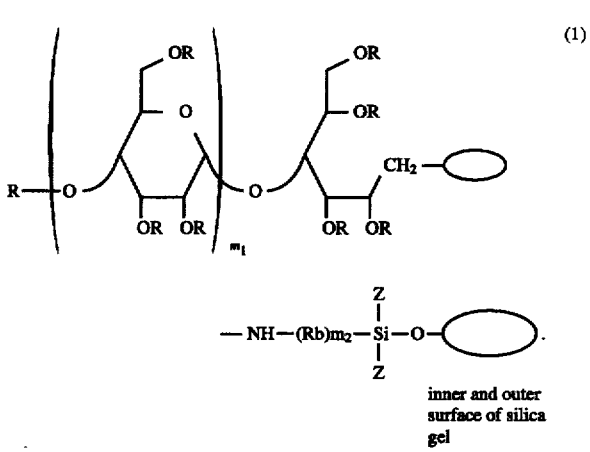

wherein
R represents anyone of —Ra, —CO—Ra and —CO—NH—Ra;

Ra represents a hydrogen atom or a substituent chosen from among a substituted or unsubstituted alkyl group, a substituted or unsubstituted phenyl group and a substituted or unsubstituted heterocyclic residue. With respect of substantially improving the separation ability the substitution rate of R is preferably 30 to 100%.

Rb represents a substituted or unsubstituted methylene group, a substituted or unsubstituted phenylene group or a group containing hetero atom(s), which is bonded to the adjacent atoms by covalent bond;

Z represents anyone chosen from among the surface of a porous carrier, a halogen atom, an alkyl group, an alkoxy group, a phenyl group, a silane agent and a saccharide-bonded silane agent;

$m_1$ represents the number of monosaccharide units and is a number of from 10 to 500 on average; and $m_2$ represents an integer of from 1 to 20.

Also provided are a method of producing the novel polysaccharide derivative of the above-mentioned general formula (1) in which a silane agent is chemically bonded to a porous carrier and thereafter a polysaccharide having degree of polymerization from 11 to 500 or its derivative is also chemically bonded to the surface-treated carrier at the reducing terminal thereof; a method of producing the novel polysaccharide derivative of the above-mentioned formula (1) in which a polysaccharide having degree of polymerization from 11 to 500 or its derivative is chemically bonded to a silane agent at the reducing terminal of the polysaccharide or its derivative and thereafter the compound is chemically bonded to a porous carrier also; and a separating agent for chromatography containing the novel polysaccharide derivative.

DETAILED DESCRIPTION OF THE INVENTION

The compound composed of a silane agent and a porous carrier that have been chemically bonded to each other, which is used for producing the novel polysaccharide derivative of the above-mentioned formula (1), may be obtained by bonding a silane agent and silica gel of a porous carrier to each other by known reaction. One means for chemically bonding a polysaccharide to a silanizing reagent at the 1-positioned carbon in the reducing terminal of the polysaccharide, is a method of forming a Schiff base by the aldehyde group and the amino group, followed by reducing the base in the presence of a reducing agent to form a secondary amine. (Refer to Glycoconjugate J. (1986) 3, 311–319, ELISABETH KALLIN et al.) (This is hereinafter referred to as a reductive amination method.) Apart from this, there are employed other various bonding modes, such as ether bonding of the following formula (A), ester bonding of the following formula (B), amide bonding of the following formula (C) and thiourethane bonding of the following formula (D), in which the polysaccharide is bonded to the porous carrier only at the 1-positioned carbon in the reducing terminal of the polysaccharide.

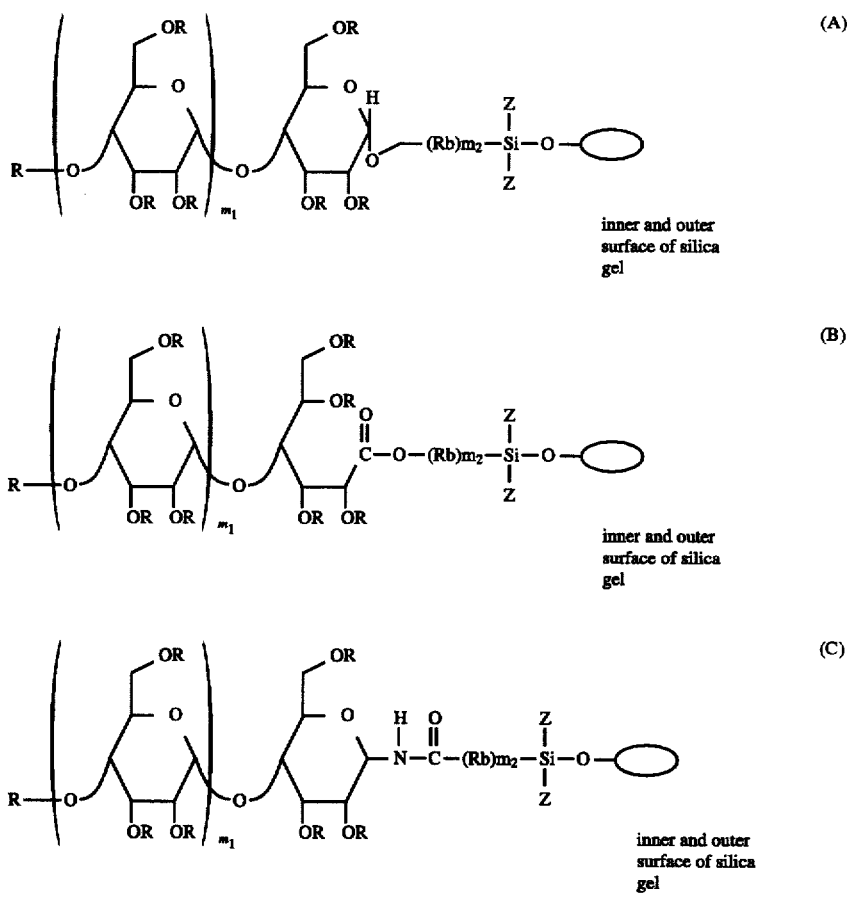

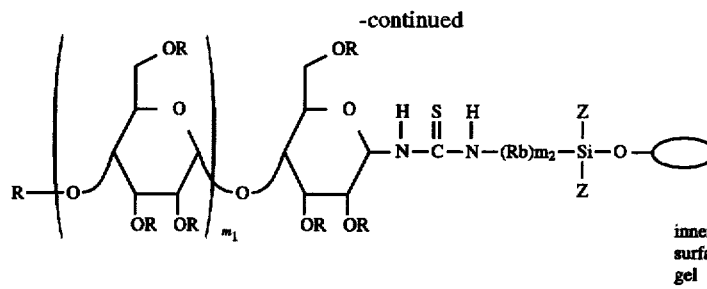

In these formulae, R, Rb, $m_1$ and $m_2$ have the same meanings as those mentioned above.

The polysaccharide to be used in the present invention may be any of synthetic polysaccharides, natural polysaccharides and polysaccharide derivatives, provided that it has a reducing terminal and is optically active. Preferred are those having a high regularity in the bonding mode. For instance, usable are α-1,4-glucan (amylose), β-1,4-glucan (cellulose), α-1,6-glucan (dextran), β-1,6-glucan (pustulan), α-1,3-glucan, β-1,3-glucan (e.g., curdlan, schizophylan, α-1,2-glucan, β-1,2-glucan, β-1,4-chitosan, β-1,4-N-acetylchitosan (chitin), β-1,4-galactan, α-1,6-galactan, β-1, 2-fructan (inulin), β-2,6-fructan (levan), β-1,4-xylan, β-1,4-mannan, α-1,6-mannan, pullulan, agarose, alginic acid, starch having a high amylose content, etc. More preferred are cellulose, amylose, β-1,4-chitosan, chitin, β-1,4-mannan, β-1,4-xylan, inulin and cardlan, from which polysaccharides having a high purity may be obtained with ease. These polysaccharides are desired to have a number average degree of polymerization 11 or more, of which the uppermost limit is not limited but is preferably 500 or less in view of the easiness in handling them.

The porous carrier to be used in the present invention may be a porous inorganic carrier or a porous organic carrier. For instance, mentioned are porous inorganic carriers such as silica gel, diatomaceous earth, porous glass, hydroxyapatite, alumina, titanium oxide, magnesia, etc.; and porous organic carriers such as polyacrylamides, polyacrylates, etc. Of these, especially preferred is silica gel. Silica gel for use in the present invention may have a particle size of from 1 to 1000 μm, preferably from 2 to 100 μm, and a mean pore size of from 1 nm to 100 μm, preferably from 2 nm to 500 nm. When a porous membrane is used as the porous carrier, it is possible to obtain a substance useful for a novel separating agent for chromatography.

Next, the silane agent for use in the present invention will be mentioned. When the reductive amination method is employed, a silane agent having amino group(s) is used, and that having primary amine(s) is preferred. As the silane agent, any of commercial silane coupling reagents and synthetic silane agents that have been modified to have amine(s) may be employed.

Also employable are spacers capable of bonding a silanizing reagent and a polysaccharide, such as those having the same or different two or more functional groups in which one functional group chemically bonds to the reducing terminal of a polysaccharide while the other functional group chemically bonds to a silane agent. As such functional groups, for example, mentioned are a vinyl group, an amino group, a hydroxyl group, a carboxyl group, an aldehyde group, an isocyanate group, a thiocyanate group, an isothiocyanate group, a thiol group, a silanol group, an epoxy group, an ether group, an ester group, an amido group, a halogen atom, etc. The silane agent to be employed in the present invention may be anyone that may bond to these functional groups, and typical examples of the silane agent are mentioned below. Rb in the above-mentioned formula (1) represents a substituted or unsubstituted methylene group, a substituted or unsubstituted phenylene group or a group containing hereto atom(s), which is bonded to the adjacent atoms by covalent bond. Typically, it corresponds to a part of the side chain of the silane agent mentioned below or to a part of the moiety formed by chemical bonding of a spacer and the silane agent.

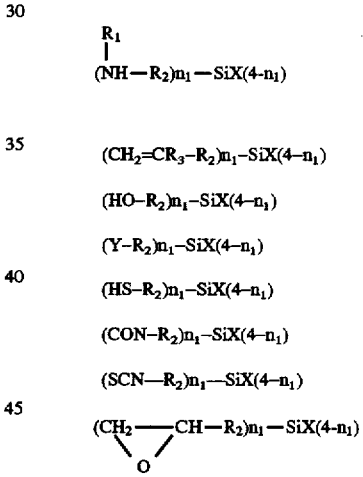

In these formulae, $n_1$ represents an integer of from 1 to 3, $R_1$ represents a hydrogen atom, an alkyl chain having from 1 to 20 or so carbon atoms or its derivative, $R_2$ represents an alkyl chain having from 1 to 20 or so carbon atoms or its derivative, at least one X represents a substituted or unsubstituted alkoxy group having from 1 to 10 carbon atoms, a halogen atom (preferably chlorine), a hydroxyl group, or a substituted or unsubstituted phenyl group, and Y represents a halogen atom.

The substituent R that is introduced into a part or all of the hydroxyl groups in the polysaccharide moiety of the following formula (2) is to modify the hydroxyl groups. Two or more different R's may be introduced into the hydroxyl groups of one molecule of the polysaccharide moiety. Ra of the substituent R is chosen from among a substituted or unsubstituted alkyl group, a substituted or unsubstituted phenyl group and a substituted or unsubstituted heterocyclic residue. Typically, it includes a methyl group, an ethyl group, a propyl group, a butyl group, a t-butyl group, a phenyl group, a methylphenyl group, a dimethylphenyl group, an ethylphenyl group, a diethylphenyl group, a trimethylphenyl group, an alkoxyphenyl group, a dialkoxyphenyl group, a halogenophenyl group, a dihalogenophenyl group, a phenylazophenyl group, a naphthyl group, an anthryl group, a pyridyl group, a furyl group, etc.

are slow to form Schiff bases while strong reducing agents will predominantly reduce carbonyl groups, weak reducing agents such as sodium borocyanohydride or the like are preferably employed. For the reductive amination, the reducing terminal of a polysaccharide may be chemically bonded to a silane agent via a spacer therebetween. Namely, it is possible that a spacer having an amino group as one functional group is allowed to react with the reducing

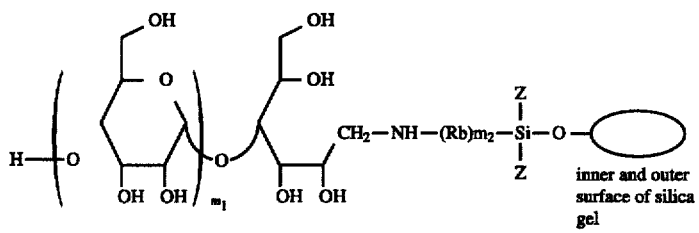

(2)

The introduction of these substituents into the hydroxyl groups in the saccharide moiety of the compound of the above-mentioned formula (2) may be effected by any known method.

Methods of producing the novel compounds of formula (1) of the present invention will be exemplified below.

Method 1:

First, a method of producing the compound of the above-mentioned formula (2) will be illustrated.

Reaction ①

The reaction for bonding a polysaccharide having a reducing terminal and a surface-treated, porous silica gel carrier will be illustrated.

For treating the inner and outer surfaces of the pores of silica gel with a silane agent having an amino group, such as 3-aminopropyl-triethoxysilane, any conventional method may be employed. The surface-treated silica gel is added to a solution prepared by dissolving a polysaccharide having a reducing terminal in a solvent such as dimethylsulfoxide (DMSO) or the like and a reducing agent is added thereto, whereupon the amino group functionalized silica gel is allowed to react with the polysaccharide at 50° to 80° C. for 12 hours so as to conjugate with them by reductive amination. During the reaction, acetic acid may be added to the reaction mixture so as to neutralize the mixture at pH of 6 to 8. The excess polysaccharide is removed by washing with a solvent such as DMSO, acetone, hexane or the like, and the reaction product is dried under reduced pressure to obtain the compound of the above-mentioned formula (2).

As the reducing agent to be used in the reaction, mentioned are borane compounds such as $NaBH_4$ (sodium borohydride), $NaBH_3CN$ (sodium borocyanohydride), borane-pyridine complex, borane-dimethylamine complex, borane-trimethylamine complex, etc. Since polysaccharides terminal of a polysaccharide by reductive amination and thereafter the other functional group of the spacer is chemically bonded to a silane agent.

Method 2:

Reaction ①

The reaction of bonding a polysaccharide having a reducing terminal to a silanizing reagent will be illustrated.

A polysaccharide having a reducing terminal is dissolved in solvent such as DMSO or the like and a silane agent having an amino group and a reducing agent are added thereto, whereupon the reducing terminal of the polysaccharide is allowed to react with the amino group at 50° to 80° C. and they are bonded together by reductive amination to obtain a compound of the following formula (3). In the method, the silane agent will often partly polymerize. In order to evade such polymerization, the reaction is preferably conducted by anhydrous water.

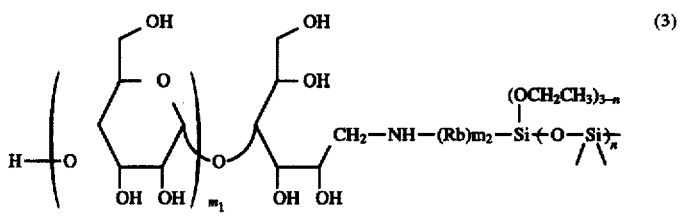

(3)

Reaction ②

The reaction of bonding the compound of formula (3) that has been produced by the above-mentioned reaction ① to silica gel will be illustrated.

The polysaccharide derivatives of the above-mentioned formula (3) that has been produced by the reaction is dissolved in DMSO, lithium chloride-dimethylacetamide (LiCl-DMA) solution or the like, pyridine as a catalyst is added thereto and an activated silica gel is added thereto, whereupon the compound of formula (3) is bonded to the porous silica gel at the silane moiety of the compound by a conventional silane-treating method to obtain the compound of the above-mentioned formula (2).

In the compound of formula (3) that is produced by Method 2, silane moiety is relatively unstable. In view of the easiness in handling the compound, therefore, Method 1 is preferred.

Method 3:

The compound of formula (2) that has been obtained in the above-mentioned Method 1 or 2 is allowed to react with, for example, 4-methylphenyl isocyanate or 3,5-dimethylphenyl isocyanate or 3,5-dichlorophenyl isocyanate or phenyl isocyanate in anhydrous DMA/LiCl/pyridine solution or anhydrous DMSO/pyridine so as to substitute all or a part of the hydroxyl groups in the saccharide moiety of the compound to give the compound of the above-mentioned formula (1). The reaction may be conducted by any known method.

The amount of the compound bonded to the silica gel is not specifically limited but is, in general, preferably from 5 to 50% by weight. In order to remove the influence of the remaining silanol group(s) in the thus-obtained compound, the compound may be subjected to end-capping treatment by a conventional method, whereby the property of the compound as a separating agent may be improved.

In illustrating the chemical structures of compounds, the partial structure indicating the positions of the hydroxyl groups in the saccharide moiety has been partly omitted or simplified herein for convenience sake so as to meet the universality of the compounds.

Next, the present invention will be explained in more detail by means of the following examples, which, however, are not intended to restrict the scope of the present invention.

EXAMPLE 1

(1-1) Production of Surface-treated Silica Gel (1-1)

12 ml of anhydrous benzene and one ml of anhydrous pyridine were added to 10 g of silica gel (produced by Fuji Silicia Co.; mean pore diameter, 50 nm; mean particle size, 5 μm) that had been previously activated (by drying in vacuum at 180° C. for 2 hours), and 0.7 ml of 3-(2-aminoethylaminopropyl)trimethoxysilane were added thereto and allowed to react at 90° C. for 12 hours.

The surface-treated silica gel was washed with methanol, acetone and hexane and then dried in vacuum at 60° C. for 2 hours to obtain a surface-treated silica gel (Silica Gel 1-1).

(1-2) Production of Surface-treated Silica Gel (1-2)

12 ml of anhydrous benzene and one ml of anhydrous pyridine were added to 10 g of silica gel (produced by Fuji Silicia Co.; mean pore diameter, 50 nm; mean particle size, 5 μm) that had been previously activated (by drying in vacuum at 180° C. for 2 hours), and 0.7 ml of 3-aminopropyltriethoxysilane were added thereto and allowed to react at 90° C. for 12 hours.

The surface-treated silica gel was washed with methanol, acetone and hexane and then dried in vacuum at 60° C. for 2 hours to obtain a surface-treated silica gel (Silica Gel 1-2).

(1-3) Production of Compound of General Formula (4)

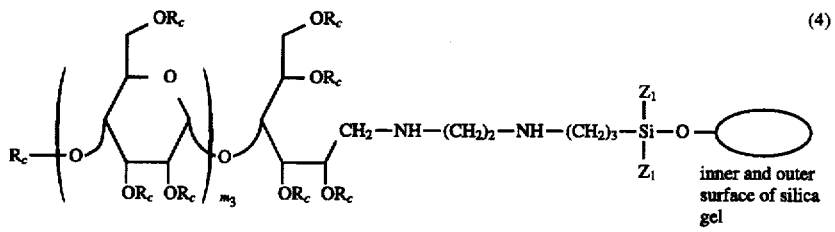

wherein

Rc represents a hydrogen atom or

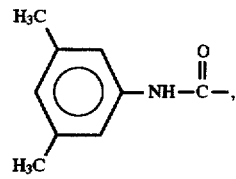

and the substitution degree of hydroxyl group was 90% or more from the weight analysis;

$m_3$ represents about 100 on average;

$Z_1$ represents any of the surface of silica gel, a methoxy group and a silane agent or a saccharide-bonded silane agent.

A solution prepared by dissolving 1.8 g of amylose (mean Dp, 100) in 8 ml of anhydrous DMSO was added to aminoethylaminopropyl functionalyzed silica gel (Silica Gel 1-1), that had been obtained in the previous step (1-1). A solution prepared by dissolving 150 mg of NaBH$_3$CN in 5 ml of anhydrous DMSO, to which 30 mg of acetic acid had been added, was added thereto and allowed to react at 50° C. for 12 hours under nitrogen, whereby the amylose was chemically bonded to amine functionalyzed silica gel at the reducing terminal of the amylose.

The thus-obtained polysaccharide-conjugated silica gel was collected by filtration through a glass filter G4, and thereafter with excess DMSO, tetrahydrofuran, methanol, acetone and hexane to remove the excess amylose and other impurities therefrom, and this was then dried in vacuum at 60° C. for 2 hours. The bonding of the polysaccharide to the silica gel was confirmed by elementary analysis (see Table 1 below). Thus, the compound of the following formula (5) was obtained. The elementary analysis gave C of 4.40%, H of 1.03% and N of 0.4%.

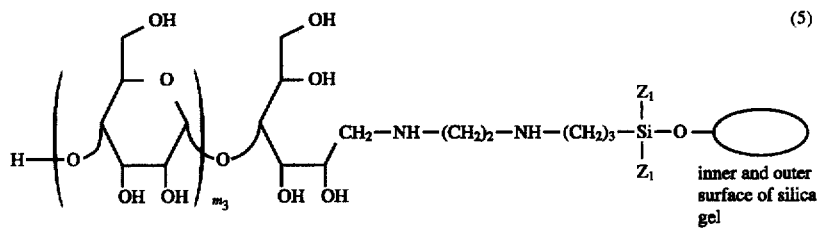

(5) inner and outer surface of silica gel

The polysaccharide-conjugated silica gel was dispersed in a solution composed of 8 ml of anhydrous DMA-LiCl and 3 ml of pyridine, and 3.0 ml of 3,5-dimethylphenyl isocyanate were added thereto and allowed to react at 80° C. for 12 hours in nitrogen whereby the hydroxyl groups in the saccharide moiety that had been chemically bonded to the surface of the silica gel were modified. After the presence of excess isocyanate groups in the reaction solution was identified by the stretching vibration between C=N appeared at 2270 $cm^{-1}$ in the IR spectrum of the solution, the polysaccharide derivative-conjugated silica gel-in the reaction solution was washed with tetrahydrofuran, methanol, acetone and hexane to thereby remove impurities therefrom and then dried in vacuum at 60° C. for 2 hours. Next, the compound was analyzed by IR spectrography and elementary analysis (see Table 1).

TABLE 1

| Separating Agent | Elementary Analysis | | |
|---|---|---|---|
| | C (%) | H (%) | N (%) |
| Formula (4) | 14.22 | 1.70 | 1.63 |
| Formula (5) | 4.40 | 1.03 | 0.40 |
| Formula (6) | 16.45 | 1.78 | 1.77 |

TABLE 1-continued

| Separating Agent | Elementary Analysis | | |
|---|---|---|---|
| | C (%) | H (%) | N (%) |
| Formula (7) | 4.29 | 0.90 | 0.22 |
| Formula (8) | 7.76 | 0.97 | 0.86 |
| Formula (9) | 2.12 | 0.56 | 0.15 |
| Formula (10) | 13.25 | 1.27 | 1.67 |
| $R^1$— (11) | 12.63 | 1.04 | 1.59 |

The IR spectrum revealed the stretching vibration of the carbonyl group (absorption by C=O in the secondary carbamate) at near 1730 $cm^{-1}$ and the elementary analysis verified the bonding of the polysaccharide to the silica gel. Accordingly, the compound of the above-mentioned general formula (4) was obtained. This is used as a separating agent for chromatography.

The compound was tested with respect to the function as the separating agent for various racemic compounds, and the test results obtained are shown in Table 2 below.

TABLE 2

| | Substance of the Invention | | Comparative | Substance of the Invention | |
|---|---|---|---|---|---|
| Formula | Formula (4) | Formula (6) | Test | Formula (10) | (Formula (11) |
| Polysaccharide | Amylose | Amylose | Amylose | Amylose | Amylose |
| Number of Plate* $t_0$ | 5400 $t_0$ = 5.61 | 4600 $t_0$ = 5.41 | — | 5200 $t_0$ = 5.50 | 4800 $t_0$ = 5.45 |
| Retention Separation | $k_1$  α | $k_1$  α | $k_1$  α | $k_1$  α | $k_1$  α |
| (structure 1) | 0.50 (+) 2.23 | 0.76 (+) 2.53 | 0.24 (+) 2.56 | 1.25 (+) 1.14 | 0.65 (+) 1.48 |
| (structure 2) | 0.69 (+) 1.38 | 1.07 (+) 1.43 | 0.40 (+) 1.56 | 2.92 (+) 1.26 | 1.05 (+) 1.30 |
| (structure 3) | 1.22 (+) 1.12 | 1.69 (+) 1.18 | 0.62 (+) 1.33 | 4.49 (+) 1.18 | 3.02 (+) 1.64 |

TABLE 2-continued

| | Substance of the Invention | | Comparative | Substance of the Invention | |
|---|---|---|---|---|---|
| Formula Polysaccharide | Formula (4) Amylose | Formula (6) Amylose | Test Amylose | Formula (10) Amylose | (Formula (11) Amylose |
| *(cyclohexanone with Ph)* | 0.80 (−) Δ | 1.20 (−) Δ | 0.45 (−) Δ | 4.36 (+) Δ | 1.80 (−) Δ |
| Co(acac)₃ | 0.39 x | 1.96 x | 0.64 (+) Δ | 6.84 x | 3.40 (−) 1.31 |
| *(Ph-C(=O)-CH(OH)-Ph)* | 3.36 (−) 1.06 | 5.17 (−) 1.13 | 1.83 (−) 1.07 | 12.07 x | 5.20 x |
| *(cyclopropane-1,2-di-CONHPh)* | 3.61 (+) 1.18 | 5.18 (+) 3.61 | 1.31 (+) 2.15 | 1.43 (+) 1.37 | 2.11 (+) 1.38 |
| $(C_6H_5)_3-C-C(OH)(C_6H_5)-H$ | 2.01 (+) 2.02 | 3.62 (+) 2.10 | 1.06 (+) 2.18 | 2.06 (+) 2.20 | 2.17 (+) 1.82 |
| *(binaphthol dimethyl)* | 2.29 (−) 1.99 | 3.75 (−) 2.07 | 1.16 (−) 1.68 | 2.14 (+) 1.15 | 1.83 (−) 1.80 |

In Table 2, $k_1$ indicates capacity factor of the isomer eluted first, which is obtained by the following equation; and α indicates the separation factor, which is obtained by the following equation. $k_2$ indicates capacity factor of the isomer eluted late and is obtained by the following equation. *: theoretical plate number against benzene α: $k_1/k_2$ $k_1$=[(retention time of the isomer eluted earlier)−(dead time)]/(dead time)

$k_2$=[(retention time of the isomer eluted later)−(dead time)]/(dead time)

(1-4) Production of Compound of Formula (6)

Rc represents a hydrogen atom or

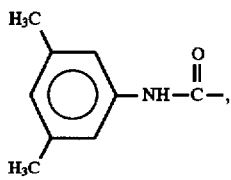

and the substitution degree of hydroxyl groups was 90% or more from the weight analysis;

$m_4$ represents about 160 on average;

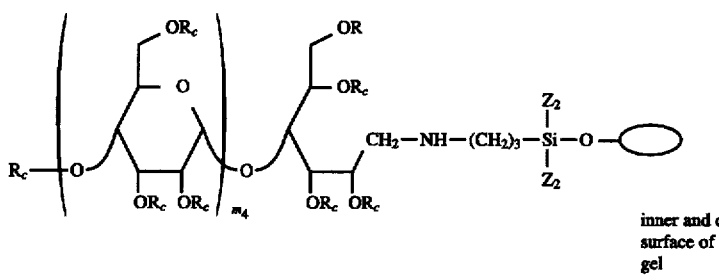

(6)

inner and outer surface of silica gel wherein $Z_2$ represents any of the surface of silica gel, an ethoxy group and a silane agent or a saccharide-bonded silane agent.

A solution prepared by dissolving 1.0 g of amylose (mean Dp, 160) in 8 ml of anhydrous DMSO was added to the aminopropyl functionalyzed silica gel (Silica Gel 1-2), that had been obtained in the previous step (1-2). A solution prepared by dissolving 150 mg of NaBH$_3$CN in 5 ml of anhydrous DMSO, to which 30 mg of acetic acid had been added, was added thereto and allowed to react at 50° C. for 12 hours under nitrogen, whereby the amylose was chemically bonded to aminopropyl functionalyzed silica gel at the reducing terminal of the amylose.

The thus-obtained polysaccharide-conjugated silica gel was collected by filtration through a glass filter G4, and was washed with DMSO, tetrahydrofuran, methanol, acetone and hexane to remove the excess amylose and other impurities therefrom, and this was then dried in vacuum at 60° C. for 2 hours. The bonding of the polysaccharide to the silica gel was confirmed by elementary analysis (see Table 1 above). Thus, the compound of the following formula (7) was obtained. The elementary analysis gave C of 4.29%, H of 0.90% and N of 0.22%.

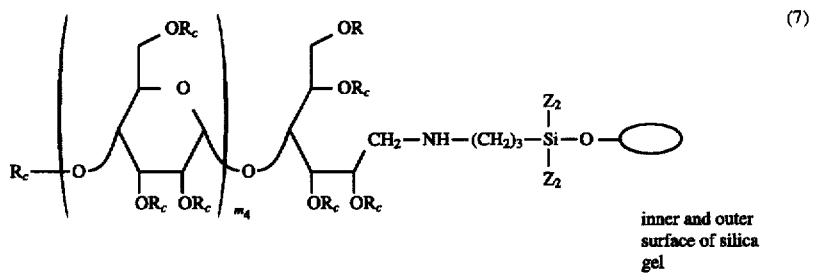

(7)

inner and outer surface of silica gel

The polysaccharide-conjugated silica gel was dispersed in a solution composed of 8 ml of anhydrous DMA-LiCl and 3 ml of pyridine, and 3.0 ml of 3,5-dimethylphenyl isocyanate were added thereto and allowed to react at 80° C. for 12 hours under nitrogen, whereby the hydroxyl groups in the saccharide moiety that had been chemically bonded to the surface of the silica gel were modified. After the presence of excess isocyanate groups in the reaction solution was identified by the stretching vibration between C=N appeared at 2270 cm$^{-1}$ in the IR spectrum of the solution, the polysaccharide derivative-conjugated silica gel in the reaction solution was washed with tetrahydrofuran, methanol, acetone and hexane to thereby remove impurities therefrom and then dried in vacuum at 60° C. for 2 hours. Next, the compound was analyzed by IR spectrography and elementary analysis (see Table 1).

The IR spectrum revealed the stretching vibration of the carbonyl group (absorption by C=O in the secondary carbamate) at near 1730 cm$^{-1}$ and the elementary analysis verified the bonding of the polysaccharide to the silica gel. Accordingly, the compound of the above-mentioned formula (6) was obtained. This is used as a separating agent for chromatography.

The compound was tested with respect to the function as the separating agent for various racemate compounds, and the test results obtained are shown in Table 2 above.

(1-5) Production of Compound of Formula (8)

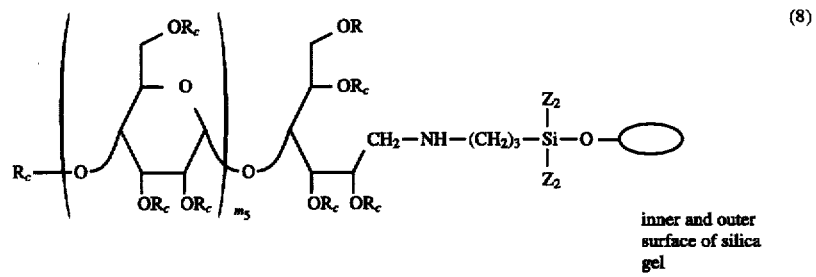

(8)

inner and outer surface of silica gel wherein

Rc represents a hydrogen atom or

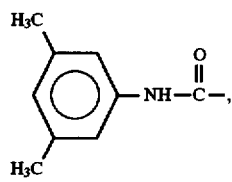

and the substitution degree of hydroxyl groups was 90% or more from the weight analysis;

$m_5$ represents about 200;

$Z_2$ represents any of the surface of silica gel, an ethoxy group and a silane agent or a saccharide-conjugated silane agent.

A solution prepared by dissolving 1.0 g of cellulose (produced by Merck Co.) in 21 ml of anhydrous DMA/LiCl was added to the aminopropyl functionalized silica gel (Silica Gel 1-2), that had been obtained in the previous step (1-2). A solution prepared by dissolving 150 mg of $NaBH_3CN$ in 5 ml of anhydrous DMSO, to which 30 mg of acetic acid had been added, was added thereto and allowed to react at 50° C. for 36 hours under nitrogen, whereby the cellulose was chemically bonded to aminopropyl functionalized silica gel at the reducing terminal of the cellulose.

The thus-obtained polysaccharide-conjugated silica gel was collected by filtration through a glass filter G4, and was washed with DMA/LiCl, tetrahydrofuran, methanol, acetone and hexane to remove the excess cellulose and other impurities therefrom, and the compound was then dried in vacuum at 60° C. for 2 hours. The bonding of the polysaccharide to the silica gel was confirmed by elementary analysis (see Table 1 above). Thus, the compound of the following formula (9) was obtained. The elementary analysis gave C of 2.12%, H of 0.56% and

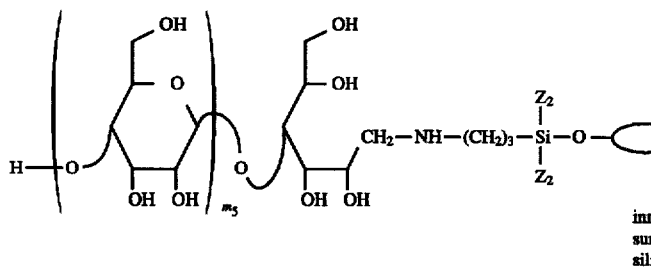

(9)

The polysaccharide-conjugated silica gel was dispersed in a solution composed of 8 ml of anhydrous DMA-LiCl and 3 ml of pyridine, and 3.0 ml of 3,5-dimethylphenyl isocyanate were added thereto and allowed to react at 80° C. for 12 hours under nitrogen, whereby the hydroxyl groups in the saccharide moiety that had been chemically bonded to the surface of the silica gel were modified. After the presence of excess isocyanate groups in the reaction solution was identified by the stretching vibration between C=N appeared at 2270 $cm^{-1}$ in the IR spectrum of the solution, the polysaccharide derivative-conjugated silica gel in the reaction solution was washed with tetrahydrofuran, methanol, acetone and hexane to thereby remove impurities therefrom and then dried in vacuum at 60° C. for 2 hours. Next, the compound was analyzed by IR spectrography and elementary analysis (see Table 1).

The IR spectrum revealed the stretching vibration of the carbonyl group (absorption by C=O in the secondary carbamate) at near 1730 $cm^{-1}$ and the elementary analysis verified the bonding of the polysaccharide to the silica gel. Accordingly, the compound of the above-mentioned formula (8) was obtained. This is used as a separating agent for chromatography.

The compound was tested with respect to the function as the separating agent for various racemic compounds, and the test results obtained are shown in Table 3 below.

TABLE 3

| Bonding Mode Polysaccharide | Formula (8) Chemical Bond Cellulose | | * Coating Cellulose | |
|---|---|---|---|---|
| Number of Plate $t_0$ | 5200 $t_0$ = 6.24 | | ** | |
| Retention Separation | $k_1$ | α | $k_1$ | α |
| ![O, Ph, Ph structure] | 0.36 | (−) 1.50 | 0.74 | (−) 1.68 |
| ![N,N bis-methylbenzyl structure] | 0.55 | (+) 1.37 | 0.97 | (+) 1.32 |
| ![cyclohexanone-Ph structure] | 0.62 | (−) 1.19 | 1.17 | (−) 1.15 |

TABLE 3-continued

| Bonding Mode Polysaccharide | Formula (8) Chemical Bond Cellulose | | * Coating Cellulose | |
|---|---|---|---|---|
| ![binaphthol dimethyl structure] | 0.83 | (−) 2.73 | 2.36 | (−) 1.83 |

* The data were derived from Yoshio Okamoto, CHEMISTRY LETTERS (1989), pp. 715 to 718.
** Not shown.

(1-6) Synthesis of Compound of the Following Formula (10)

[Compound 30]

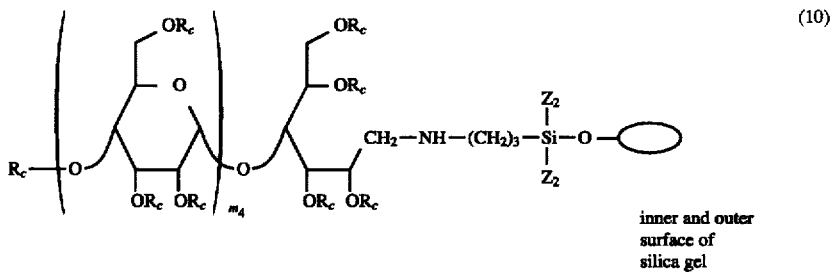

wherein

Rc represents a hydrogen atom or

[Compound 31]

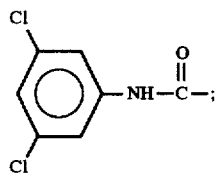

substitution rate based on the calculation of weight is 90% or above;

$m_4$ is about 170 on average; and $Z_2$ represents any of the surface of silica gel, a methoxy group, a silane agent and a saccharide-bonded silane agent.

To 3 g of the aminopropyl functionalized silica gel (Silica Gel 1-2), that had been obtained in the above step (1-2), added was a solution obtained by dissolving 1.0 g of amylose (mean Dp: 160) in 8 ml of anhydrous DMSO, and dispersed. In addition, a solution obtained by dissolving 150 mg of NaBH$_3$CN in 5 ml of anhydrous DMSO, to which added was 30 mg of acetic acid, was added to the resulting dispersion and allowed to react at 50° C. for 12 hours under nitrogen, whereby the cellulose was chemically bonded to aminopropyl functionalized silica gel at the reducing terminals of the amylose.

The thus obtained polysaccharide-conjugated silica gel was collected by filtration through a G4 glass filter, and was washed with DMSO, tetrahydrofuran, methanol, acetone and hexane to remove the excess amylose, etc. and the compound was then dried in vacuum at 60° C. for 2 hours.

The polysaccharide-conjugated silica gel was dispersed into a mixture of 8 ml of anhydrous DMA-LiCl and 3 ml of pyridine, and 5 g of 3, 5-dichlorophenyl isocyanate (this was formed from 3,5-dichloroaniline by an ordinary method) dissolved in 5 ml of DMA were added thereto and allowed to react at 80° C. for 12 hours under nitrogen, whereby the hydroxyl groups in the saccharide moiety that had been chemically bonded to the surface of the silica gel were modified. The presence of excess isocyanate groups in the reaction mixture was confirmed by the peak of C=N stretching vibration at 2,270 cm$^{-1}$ in the IR spectrum of the solution. The polysaccharide derivative-conjugated silica gel in the reaction mixture was washed with tetrahydrofuran, methanol, acetone and hexane to remove impurities therefrom and then dried in vacuum at 60° C. for 2 hours. Then, the compound was analyzed by IR spectrography and elementary analysis (see Table 1).

The bonding of the polysaccharide to the silica gel, or the production of the compound of Formula (10) set forth above was confirmed by the carbonyl stretching vibration (absorption of C=O in the secondary carbamate) at near 1,730 cm$^{-1}$ in its IR spectrum, as well as by elementary analysis. The compound was tested and evaluated with respect to its function as a chromatographic separating agent for various racemic compounds. Results obtained are shown in Table 2 above.

(1-7) Synthesis of Compound of the Following Formula (11)

[Compound 32]

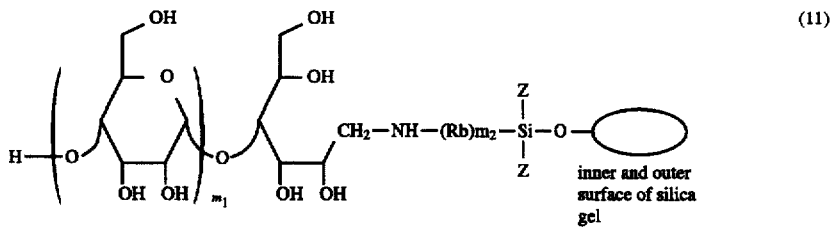

wherein

Rc represents a hydrogen atom or

[Compound 33]

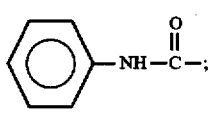

substitution degree of hydroxyl groups was 90% or more from the weight analysis;

$m_4$ is about 170 on average; and $Z_2$ represents any of the surface of silica gel, a methoxy group, a silane agent and a saccharide-bonded silane agent.

To 3 g of the aminopropyl functionalized silica gel (Silica Gel 1-2), that had been obtained in the above step (1-2), added was a solution obtained by dissolving 1.0 g of amylose (mean Dp: 160) in 8 ml of anhydrous DMSO, and dispersed. In addition, a solution obtained by dissolving 150 mg of $NaBH_3CN$ in 5 ml of anhydrous DMSO, to which added was 30 mg of acetic acid, was added to the resulting dispersion and allowed to react at 50° C. for 12 hours under nitrogen, whereby the amylose was chemically bonded to aminopropyl functionalized silica gel at the reducing terminal of the amylose.

The thus obtained polysaccharide-conjugated silica gel was collected by filtration through a glass filter G4, and was washed with DMSO, tetrahydrofuran, methanol, acetone and hexane to remove the excess amylose, etc. and this was then dried in vacuum at 60° C. for 2 hours.

The saccharide-bonded silica gel was dispersed into a mixture of 8 ml of anhydrous DMA-LiCl and 3 ml of pyridine, and 2 ml of phenyl isocyanate were added thereto and reacted at 80° C. for 12 hours under nitrogen, whereby the hydroxyl groups in the saccharide moiety chemically bonded to the surface of the silica gel were modified. The presence of excess isocyanate groups in the reaction mixture was confirmed by the peak of C=N stretching vibration at 2,270 $cm^{-1}$ in its IR spectrum. The polysaccharide derivative-conjugated silica gel in the reaction mixture was washed with tetrahydrofuran, methanol, acetone and hexane to remove impurities therefrom and then dried in vacuum at 60° C. for 2 hours. Then, the compound was analyzed by IR spectrography and elementary analysis (see Table 1).

The bonding of the polysaccharide to the silica gel, or the production of the compound of Formula (11) set forth above was confirmed by the carbonyl stretching vibration (absorption of C=O in the secondary carbamate) at near 1,730 $cm^{-1}$ in its IR spectrum, as well as by elementary analysis. The compound was tested and evaluated with respect to its function as a chromatographic separating agent for various racemic compounds. Results obtained are shown in Table 2 above.

USE EXAMPLE

Preparation of Column for Chiral Resolution and Chiral Resolution Ability

The novel compound obtained in (1-3) of Example 1 was packed into an empty, stainless steel column of 0.46×25 cm, by a slurry packing method. The packing device used was PS-10;PS-20 Auto Packing System manufactured by Kyoto Chromato Co. Using the column, the chiral resolution ability of the compound was evaluated. The high performance liquid chromatography system used comprised Waters 510 Pump and 486 UV Detector. As the comparative sample, used was a separating agent that was previously prepared amide bond between lactonated amylose and a surface-treated silica gel (Japanese Patent Application No. 135170/1993).

To examine the solvent resistance of the chiral resolution column packed with the compound of the present invention, a tetrahydrofuran (THF) solution was passed through the column at a flow rate of 1 ml/min for 2 hours and thereafter the chiral resolution ability of the column was measured with the result that no change was recognized. The result of the examination verified the excellent solvent resistance of the compound tested.

The analysis was carried out, using an eluent of hexane/IPA (=90/10) while # was 95:5. The flow rate was 0.5 ml/min and the temperature was room temperature. As has been explained hereinabove, the novel substances of the present invention have excellent solvent resistance and are useful as a separating agent for chiral resolution of chiral compounds. According to the present invention, the novel substances are produced efficiently.

While the invention has been described in detail and with reference to specific embodiments thereof, it will be apparent to one skilled in the art that various changes and modifications can be made therein without departing from the spirit and scope thereof.

What is claimed is:

1. A chromatography matrix comprising a polysaccharide compound which is chemically bonded to an inner surface and an outer surface of the pores of a porous carrier at a reducing terminal of the polysaccharide compound, the composition having the following formula (1):

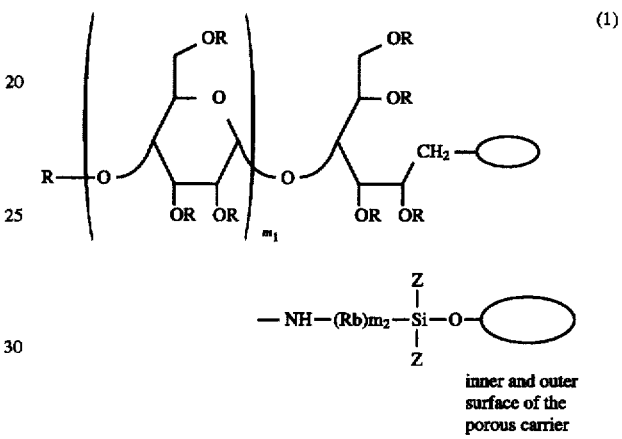

inner and outer surface of the porous carrier wherein
each R is independently —Ra, —CO—Ra or —CO—NH—Ra;
Ra represents a hydrogen atom or a substituent selected from the group consisting of a substituted alkyl group, an unsubstituted alkyl group, a substituted phenyl group, an unsubstituted phenyl group, a substituted heterocyclic residue and an unsubstituted heterocyclic residue;
Rb represents a substituted or unsubstituted methylene group, a substituted or unsubstituted phenylene group or a group containing one or more hereto atoms, which is bonded to adjacent atoms by a covalent bond;
Z is selected from the group consisting of a surface of a porous carrier, a halogen atom, an alkyl group, an alkoxy group, a phenyl group and a silane agent;
$m_1$ represents the mean degree of polymerization and is a number from 10 to 500 and
$m_2$ represents an integer from 1 to 20.

2. The chromatography matrix as claimed in claim 1, wherein the polysaccharide compound is selected from the group consisting of amylose, cellulose, dextran, postulan, α-1,3-glucan, β-1,3-glucan, α-1,2-glucan, β-1,2-glucan, β-1,4-chitosan, chitin, β-1,4-galactan, α-1,6-galactan, inulin, curdlan levan, β-1,4-xylan, β-1,4-mannan, α-1,6-mannan, pullulan, agarose, alginic acid and starch having a high amylose content.

3. The chromatography matrix as claimed in claim 1, wherein the porous carrier is selected from the group consisting of silica gel, diatomaceous earth, porous glass, hydroxyapatite, alumina, titanium oxide, magnesia, polyacrylamide and polyacrylate.

4. The chromatography matrix as claimed in claim 1, wherein the porous carrier is silica gel having a particle size of 1 to 1000 μm and a mean pore size of 1 nm to 100 μm.

5. The chromatography matrix as claimed in claim 1, wherein Z is a silane agent selected from the group consisting of

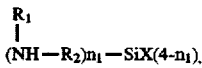

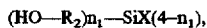

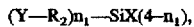

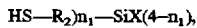

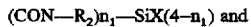

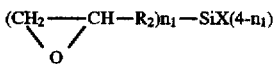

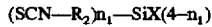

wherein $n_1$ represents an integer of from 1 to 3, $R_1$ represents a hydrogen atom or an alkyl chain having from 1 to 20 carbon atoms $R_2$ represents an alkyl chain having from 1 to 20 carbon atoms, at least one X represents a substituted or unsubstituted alkoxy group having from 1 to 10 carbon atoms, a halogen atom, a hydroxyl group, or a substituted or unsubstituted phenyl group, and y represents a halogen atom.

6. The chromatography matrix composition as claimed in claim 1, wherein Ra is selected from the group consisting of a methyl group, an ethyl group, a propyl group, a butyl group, a phenyl group, a methylphenyl group, a dimethylphenyl group, an ethylphenyl group, a diethylphenyl group, a trimethylphenyl group, an alkoxyphenyl group, a dialkoxyphenyl group, a halogenophenyl group, a dihalogenophenyl group, a phenylazophenyl group, a naphthyl group, an anthryl group, a pyridyl group and a furyl group.

7. The chromatography matrix as claimed in claim 6, wherein Ra is a t-butyl group.

8. The chromatography matrix as claimed in claim 1, wherein said porous carrier is silica gel and the polysaccharide is in an amount of 5 to 50% by weight.

9. The chromatography matrix as claimed in claim 1, wherein the polysaccharide is selected from the group consisting of amylose and cellulose; R is —CO—NH—Ra, Ra is 3,5-dimethylphenyl and $m_1$ is 90 to 500.

10. The chromatography matrix as claimed in claim 9, wherein Rb is $CH_2$, $m_2$ is 3 and Z is $OCH_2CH_3$.

11. The chromatography matrix as claimed in claim 9, wherein Rb is $(CH_2)_2$—NH—$(CH_2)_3$, $m_2$ is 1 and Z is $OCH_3$.

12. A method of producing a chromatography matrix comprising a polysaccharide compound of the formula (1) as claimed in claim 1 comprising:

(a) reacting a silane agent with a porous carrier to chemically bond the silane agent to the porous carrier, (b) reacting a polysaccharide having a degree of polymerization from 11 to 500 with the porous carrier bound to the silane agent from step (a) to chemically bind the porous carrier at a reducing terminal of the polysaccharide and (c) reacting the polysaccharide bonded to the porous carrier from step (b) with a compound to replace one or more hydrogen atoms in one or more hydroxyl groups in the polysaccharide with a group of the formula Ra, —CO—Ra or —CO—NH—Ra, wherein Ra is selected from the group consisting of an unsubstituted alkyl group, a substituted alkyl group, an unsubstituted phenyl group, a substituted phenyl group, an unsubstituted heterocyclic residue and a substituted heterocyclic residue.

13. The method as claimed in claim 12, wherein the compound in step (c) is selected from the group consisting of 4-methylphenyl isocyanate; 3,5-dimethylphenyl isocyanate; 3,5-dichlorophenyl isocyanate; and phenyl isocyanate, and step (c) is carried out in the presence of anhydrous DMA/LiCl/pyridine solution or anhydrous DMSO/pyridine.

14. A method of producing a chromatography matrix comprising a polysaccharide compound of the formula (1) as claimed in claim 1 comprising:

(a) reacting a polysaccharide having a degree of polymerization from 11 to 500 with a silane agent to chemically bond the polysaccharide to the silane agent at a reducing terminal of the polysaccharide, (b) reacting the polysaccharide bound to the silane agent from step (a) with a porous carrier to chemically bond the polysaccharide to the porous carrier and (c) reacting the polysaccharide bonded to the porous carrier from step (b) with a compound to replace one or more hydrogen atoms in one or more hydroxyl groups in the polysaccharide with a group of the formula Ra, —CO—Ra or —CO—NH—Ra, wherein Ra is selected from the group consisting of an unsubstituted alkyl group, a substituted alkyl group, an unsubstituted phenyl group, a substituted phenyl group, an unsubstituted heterocyclic residue and a substituted heterocyclic residue.

15. The method as claimed in claim 14, wherein the compound in step (c) is selected from the group consisting of 4-methylphenyl isocyanate; 3,5-dimethylphenyl isocyanate; 3,5-dichlorophenyl isocyanate; and phenyl isocyanate, and step (c) is carried out in the presence of anhydrous DMA/LiCl/pyridine solution or anhydrous DMSO/pyridine.

16. In a chromatography separation method including passing a material to be separated through a column packed with a separating agent for chromatography, wherein the improvement is the use of the chromatography matrix according to claim 1.

17. A chromatography matrix comprising a polysaccharide compound which is chemically bonded to a porous carrier, the composition having a structure selected from the group consisting of

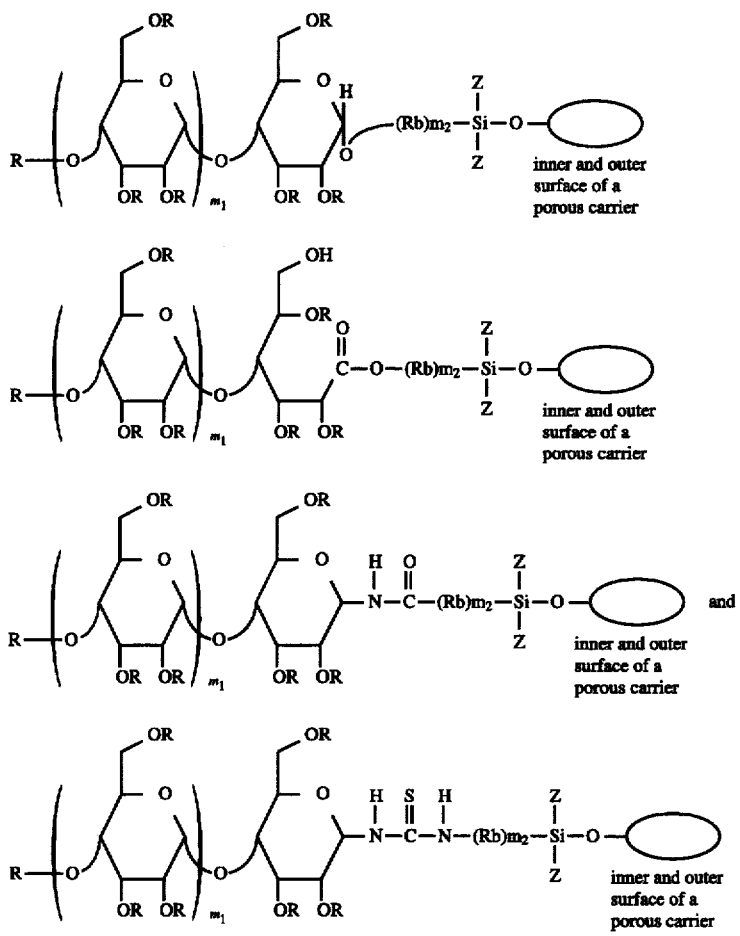

wherein

R represents —Ra, —CO—Ra or —CO—NH—Ra;

Ra represents a hydrogen atom or a substituent selected from the group consisting of a substituted alkyl group, an unsubstituted alkyl group, a substituted phenyl group, an unsubstituted phenyl group, a substituted heterocyclic residue and an unsubstituted heterocyclic residue;

Rb represents a substituted or unsubstituted methylene group, a substituted or unsubstituted phenylene group or a group containing one or more hetero atoms, which is bonded to adjacent atoms by a covalent bond;

Z represents a surface of a porous carrier, a halogen atom, an alkyl group, an alkoxy group, a phenyl group and a silane agent;

$m_1$ represents the mean degree of polymerization and is a number from 10 to 500 and $m_2$ represents an integer from 1 to 20.

18. In a chromatography separation method including passing a material to be separated through a column packed with a separating agent for chromatography, wherein the improvement is the use of the chromatography matrix according to claim 17.

\* \* \* \* \*

UNITED STATES PATENT AND TRADEMARK OFFICE
CERTIFICATE OF CORRECTION

PATENT NO. : 5,679,572
DATED : October 21, 1997
INVENTOR(S) : Okamoto et al

Page 1 of 2

It is certified that error appears in the above-identified patent and that said Letters Patent is hereby corrected as shown below:

In the Title Page, right column, in the ABSTRACT, structural formula (1): after "$CH_2$-" delete

Column 2, formula (1): between lines 30-40, after "$CH_2$" delete

Column 12, line 24, "$R^1$-(11)" should be --Formula (11)--.

Columns 15 and 16, bottom of page, formula (8) should be deleted and replaced with the following formula (8):

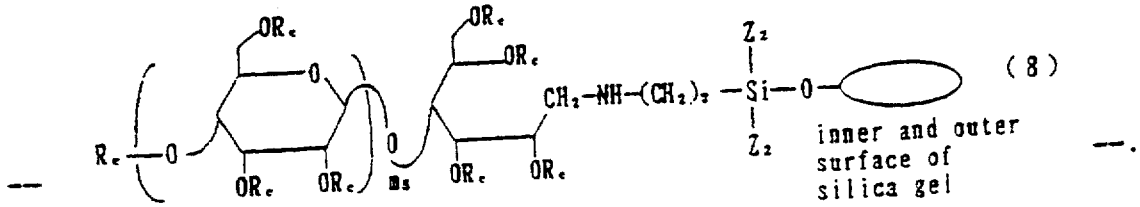

UNITED STATES PATENT AND TRADEMARK OFFICE
CERTIFICATE OF CORRECTION

PATENT NO. : 5,679,572
DATED : October 21, 1997
INVENTOR(S) : Okamoto et al

It is certified that error appears in the above-identified patent and that said Letters Patent is hereby corrected as shown below:

Column 22, formula (1): between lines 17-26, after "$CH_2$" delete

.

Signed and Sealed this

Seventeenth Day of August, 1999

Attest:

Attesting Officer

Q. TODD DICKINSON

Acting Commissioner of Patents and Trademarks